United States Patent [19]

Salinaro

[11] Patent Number: 5,567,626
[45] Date of Patent: Oct. 22, 1996

[54] METHOD OF DETECTING BIOLOGICAL MATERIALS USING A POLYVINYLLIDENE FLUORIDE MEMBRANE

[75] Inventor: Richard F. Salinaro, Hastings on Hudson, N.Y.

[73] Assignee: Pall Corporation, East Hills, N.Y.

[21] Appl. No.: 420,218

[22] Filed: Apr. 11, 1995

[51] Int. Cl.⁶ .................................................. G01N 21/77
[52] U.S. Cl. ........................... 436/178; 436/86; 436/164; 436/166; 436/168; 436/169; 436/531; 435/6
[58] Field of Search .......................... 436/86, 164, 166, 436/168, 169, 178, 531; 435/6

[56] References Cited

U.S. PATENT DOCUMENTS

| | | | |
|---|---|---|---|
| 4,302,204 | 11/1981 | Wahl et al. | 23/230.3 |
| 4,341,605 | 7/1982 | Bachot et al. | 204/296 |
| 4,455,370 | 6/1984 | Bartelsman et al. | 435/6 |
| 4,618,533 | 10/1986 | Steuck | 428/315.2 |
| 4,923,620 | 5/1990 | Pall | 210/767 |
| 5,004,543 | 4/1991 | Pluskal et al. | 210/490 |
| 5,071,909 | 12/1991 | Pappin et al. | 525/54.1 |
| 5,079,272 | 1/1992 | Allegrezze, Jr. et al. | 521/134 |
| 5,183,607 | 2/1993 | Beall et al. | 264/41 |
| 5,196,508 | 3/1993 | Sipsas | 528/503 |
| 5,198,505 | 3/1993 | Sipsas et al. | 525/326.2 |
| 5,200,312 | 4/1993 | Oprandy | 435/5 |
| 5,234,809 | 8/1993 | Boom et al. | 435/91 |
| 5,240,615 | 8/1993 | Fishman | 210/651 |
| 5,283,186 | 2/1994 | Cunningham et al. | 436/531 |
| 5,284,560 | 2/1994 | Kouno et al. | 204/182.8 |

OTHER PUBLICATIONS

Towbin et. al. "Electrophoretic transfer of Proteins from polyacrylamide gels to nitrocellulose sheets: Procedure & some applications", Proc. Natl. Acd. Sci, USA 76, 4350–4354 (1979).

Thomas, "Hybridization of denetured RNA & small DNA fragments transferred to nitrocellulose", Proc. Natl. Acad. Sci. USA 77 5201–5205 (1980).

Southern, "Detection of Specific Sequences Among DNA Fragments Separated by Gel Electrophoresis", J. Mol. Biol. 98 503–517 (1975).

*Primary Examiner*—Jill Warden
*Assistant Examiner*—Sharidan Carrillo
*Attorney, Agent, or Firm*—Leydig, Voit & Mayer, Ltd.

[57] ABSTRACT

The present invention provides an improved method of detecting or transferring a biological material whereby a biological material is adhered to a membrane which is then contacted with a detecting reagent, wherein the improvement comprises utilizing a polyvinylidene fluoride membrane which has been subjected to a temperature of at least about 80° C. but less than the temperature at which the membrane softens and deforms for a time sufficient to reduce the ability of the detecting reagent to directly adhere to the membrane.

18 Claims, No Drawings

METHOD OF DETECTING BIOLOGICAL MATERIALS USING A POLYVINYLLIDENE FLUORIDE MEMBRANE

TECHNICAL FIELD OF THE INVENTION

The present invention relates to an improvement in a method of detecting biological materials, e.g., proteins, using a porous membrane. The improved method involves the use of a heat-treated polyvinylidene fluoride membrane.

BACKGROUND OF THE INVENTION

Membranes are used in a variety of methods for detecting or transferring biological materials, such as western blotting (for proteins), northern blotting (for RNA), and southern blotting (for DNA). In these various detection or transfer methods, the biological material of interest adheres to the membrane, e.g., a polyvinylidene fluoride membrane, which is then typically subjected to a detecting reagent, e.g., a dye or stain, which preferentially adheres to the biological material of interest so as to enable detection of the biological material. Many detecting reagents, however, also generally adhere, at least to some extent, to the porous membrane, particularly a polyvinylidene fluoride membrane, thereby increasing the background noise and decreasing the sensitivity or signal-to-noise ratio for detecting the biological material of interest.

Thus, there remains a need for improving those methods of detecting biological materials which utilize membranes in conjunction with detecting reagents, particularly by reducing the tendency of detecting reagents to adhere directly to such membranes. The present invention provides such an improvement through the use of a modified polyvinylidene fluoride membrane which exhibits reduced background noise. These and other objects and advantages of the present invention, as well as additional inventive features, will be apparent from the description of the invention provided herein.

BRIEF SUMMARY OF THE INVENTION

The present invention provides an improved method of detecting or transferring a biological material whereby a biological material is adhered to a membrane which is then contacted with a detecting reagent, wherein the improvement comprises utilizing a polyvinylidene fluoride membrane which has been subjected to a temperature of at least about 80° C. but less than the temperature at which the membrane softens and deforms for a time sufficient to reduce the ability of the detecting reagent to directly adhere to the membrane.

DESCRIPTION OF THE PREFERRED EMBODIMENTS

The present invention involves the use of a heat-treated polyvinylidene fluoride membrane in a method of detecting or transferring a biological material. In particular, the present invention provides for the use of a heat-treated polyvinylidene fluoride membrane in a method of detecting or transferring a biological material whereby a biological material is adhered to the membrane which is then contacted with a detecting reagent. Such detecting reagents include dyes, stains, and the like.

Suitable such methods include western blotting, northern blotting, and southern blotting. Western blotting is a method for detecting or transferring proteins and is generally described in Towbin et al., *Proc. Natl. Acad. Sci. USA,* 76, 4350–4354 (1979). Northern blotting is a method for detecting or transferring RNA's and is generally described in Thomas, *Proc. Natl. Acad. Sci. USA,* 77, 5201–5205 (1980). Southern blotting is a method for detecting or transferring DNA's and is generally described in Southern, *J. Mol. Biol.,* 98, 503–517 (1975). These detection or transfer methods, as well as numerous variations thereon and other detection or transfer procedures utilizing membranes, particularly hydrophobic membranes such as polyvinylidene fluoride membranes, are well-known in the art.

The present invention has particular applicability to protein detection or transfer methods, such as western blotting, inasmuch as proteins readily adhere to polyvinylidene fluoride membranes. Indeed, non-heat-treated polyvinylidene fluoride membranes are commercially available as FluoroTrans™ membranes (Pall Corporation, East Hills, N.Y.) for use in western blotting procedures. The heat-treated polyvinylidene fluoride membrane is desirably utilized in place of a non-heat-treated polyvinylidene fluoride membrane in western blotting procedures, as well as in any other such detection or transfer procedure wherein a non-heat-treated polyvinylidene fluoride membrane is or can be utilized to some extent.

The polyvinylidene fluoride membrane can be prepared in any suitable manner, e.g., by using the wet casting procedure described in U.S. Pat. No. 4,340,479. Any suitable polyvinylidene fluoride may be used, such as Kynar® 761 resin (Atochem, Philadelphia, Pa.). The polyvinylidene fluoride will typically have a molecular weight of at least about 5,000 daltons, preferably a molecular weight of at least about 10,000 daltons.

The polyvinylidene fluoride membrane can have any suitable porosity. The membrane will typically have a pore rating of about 10 µm or less, more typically about 1 µm or less, e.g., about 0.01–1 µm, and most typically about 0.50 µm or less. Preferably, the membrane has a pore rating of about 0.05–0.45 µm or, even more preferably, about 0.05–0.2 µm.

The polyvinylidene fluoride membrane can be heat-treated, or annealed, in any suitable manner, desirably at a temperature and for a period of time sufficient to reduce the ability of the detecting reagent to directly adhere to the membrane. In other words, the heat-treatment preferably results in a polyvinylidene fluoride membrane to which the detecting reagent is less likely to adhere as compared to the non-heat-treated polyvinylidene fluoride membrane.

Preferably, the polyvinylidene fluoride membrane is heated to a temperature of at least about 80° C. for a time sufficient to achieve the desired reduced adherence of the detecting reagent to the membrane. Of course, the membrane should not be heated at so high a temperature that the membrane becomes soft and deforms, either under its own weight or due to tension from any mechanical means by which the membrane is supported during the heating process. Typically, the upper temperature limit will be about 160° C. The amount of time of heating will vary with the heating temperature and nature of the membrane being heated. For example, small pieces of membrane in flat sheet form which are in direct contact with a high temperature surface may require only a brief exposure, e.g., less than one minute, to heat, while a rolled membrane of several hundred linear meters may require many hours of heating at low temperature for the membrane to reach a suitable equilibrium temperature.

Thus, the membrane is preferably subjected to a temperature of about 80° C. to about 160° C. for a suitable period of time, preferably for about 5 minutes to about 64 hours, with the desirable time period generally decreasing as the temperature is increased. Accordingly, the membrane is preferably subjected to about 80° C. for about 48 hours or more, more preferably about 64 hours or more. Similarly, the membrane is preferably subjected to about 160° C. for about 5 minutes or more, more preferably about 10 minutes or more.

Preferably, the polyvinylidene fluoride membrane is subjected to a temperature of about 80° C. to about 150° C., more typically a temperature of about 100° C. to about 150° C., for a suitable period of time, desirably about 32 hours or more. More preferably, the membrane is subjected to a temperature of about 120° C. to about 150° C. for a suitable period of time, desirably about 16 hours or more, e.g., about 48–72 hours. Most preferably, the membrane is subjected to a temperature of about 135° C. to about 145° C., e.g., about 140° C., for a suitable period of time, desirably about 12 hours or more, more desirably about 24 hours or more, e.g., about 36–64 hours, especially about 48 hours.

The heat-treatment of the polyvinylidene fluoride membrane can be effected without the membrane being restrained; however, the membrane preferably is dimensionally restrained during the heat-treatment so as to minimize or avoid dimensional changes in the membrane, e.g., shrinkage. Any suitable means can be used to dimensionally restrain the membrane. For example, the membrane can be placed into a frame or can be wound onto a core or roll, preferably with an interleaved material, such as a fibrous nonwoven material, to prevent layer-to-layer contact of the membrane. Most preferably, the membrane is heat-treated in roll form interleaved with a polyester fibrous nonwoven material.

The heat-treatment can be carried out by any suitable means. For example, the polyvinylidene fluoride can be subjected to the aforesaid temperature by contacting the membrane with a heated surface. Alternatively, the membrane can be subjected to the desired temperature by placing the membrane, preferably in roll form, in a suitable oven, e.g., a circulating air oven.

The heat-treatment of polyvinylidene fluoride membranes is more fully described in U.S. Pat. Nos. 5,196,508 and 5,198,505. Those patents also describe certain improvements in surface modifications which can be obtained (and are desirably exhibited by the polyvinylidene fluoride membranes in the context of the present invention) by heat-treating polyvinylidene fluoride membranes, albeit without an appreciation of the surprisingly reduced tendency of detecting reagents to adhere to such membranes in the context of the present invention.

A comparison of polyvinylidene fluoride membranes before and after heat-treatment has led to the discovery that the heat-treatment reduces the surface area of the membrane (as determined by BET analysis). While not seeking to be bound to any particular theory explaining the surprisingly reduced tendency of detecting reagents to adhere to a heat-treated polyvinylidene fluoride membrane in the context of the present invention, it is believed that the reduced tendency of detecting reagents to adhere to the heat-treated polyvinylidene fluoride membrane is at least in part the result of the reduced surface area of the heat-treated membrane. Detecting reagents apparently have a greater difficulty in adhering to the reduced-surface area polyvinylidene fluoride membrane, while the ability of biological materials, such as proteins, to adhere to the polyvinylidene fluoride membrane is not significantly altered. Thus, the background noise level is decreased, while improving the sensitivity or signal-to-noise ratio of the overall process.

The following examples further illustrate the present invention and, of course, should not be construed as in any way limiting its scope.

EXAMPLE 1

This example illustrates the superiority of the present inventive method utilizing a heat-treated polyvinylidene fluoride membrane as compared to the same method utilizing a non-heat-treated polyvinylidene fluoride membrane.

A western transfer of a standard test protein mixture from a gel to a membrane was carried out using a non-heat-treated polyvinylidene fluoride membrane (specifically, FluoroTrans™ from Pall Corporation) and the same membrane which had been subjected in roll form to about 140° C. in an air circulating oven for about 48 hours (including the heat-up and cool-down time for the oven). The general protein transfer protocol set forth in the product insert for FluoroTrans™ was followed, using amido black stain as the detecting reagent. The respective membranes were then evaluated with a densitometer.

The background intensity level (i.e., noise level) for the non-heat-treated polyvinylidene fluoride membrane was nearly twice that for the heat-treated polyvinylidene fluoride membrane. Moreover, the ratio of the intensity of the highest peak to the background level was about 1.5:1 for the non-heat-treated polyvinylidene fluoride membrane and about 2.8:1 for the heat-treated polyvinylidene fluoride membrane. Thus, the reduction in the background intensity level was accompanied by an improvement in the signal-to-noise ratio of about 100%.

EXAMPLE 2

This example further illustrates the superiority of the present inventive method utilizing a heat-treated polyvinylidene fluoride membrane as compared to commercially available protein transfer membranes.

Dyed protein markers were electrophoresed and transferred to (a) a non-heat-treated polyvinylidene fluoride membrane having a pore rating of 0.2 μm (specifically, FluoroTrans™ from Pall Corporation), (b) a heat-treated polyvinylidene fluoride membrane having a pore rating of 0.2 μm (specifically, FluoroTrans™ from Pall Corporation subjected in roll form to about 140° C. in an air circulating oven for about 48 hours (including the heat-up and cool-down time for the oven)), (c) a similarly heat-treated polyvinylidene fluoride membrane having a pore rating of 0.45 μm, (d) a commercially-available, competitive polyvinylidene fluoride protein-transfer membrane having a pore rating of 0.45 μm, and (e) a commercially-available, competitive nitrocellulose membrane having a pore rating of 0.45 μm.

A polyvinylidene fluoride capture membrane was placed behind each of the membranes being evaluated so as to capture any protein which passed through the evaluated membranes and to thereby detect any protein "burn through." The protein transfer was allowed to proceed for 24 hours, and then the capture membranes were examined for the presence of proteins.

The non-heat-treated 0.2 μm pore rated polyvinylidene fluoride membrane (sample a) exhibited no significant protein "burn through." Similarly, the heat-treated 0.2 μm pore rated polyvinylidene fluoride membranes (sample b) exhibited no significant protein "burn through." These results demonstrate that the heat-treatment process does not adversely affect the excellent properties of polyvinylidene fluoride membranes of relatively small pore rating as regards protein "burn through."

As regards the other membranes which were evaluated, the commercially-available competitive 0.45 μm pore rated polyvinylidene fluoride membrane (sample d) exhibited a small, but significant, amount of protein "burn through," while the competitive 0.45 μm pore rated nitrocellulose membrane (sample e) exhibited a high degree of protein "burn through." In contrast, the heat-treated 0.45 μm pore rated polyvinylidene fluoride membrane (sample c) exhibited no significant protein "burn through." These results demonstrate that the present inventive method results in at least an equivalent, if not lower, level of protein "burn through" as compared to methods utilizing similar pore-rated, commercially-available, competitive membranes. As a result, the present inventive method can be expected to result in at least as good, if not better, protein retention, and ultimately greater sensitivity, than methods involving those commercially-available, competitive membranes which were evaluated herein.

All of the references cited herein are hereby incorporated in their entireties by reference.

While this invention has been described with an emphasis upon preferred embodiments, it will be obvious to those of ordinary skill in the art that variations of the preferred products and methods may be used and that it is intended that the invention may be practiced otherwise than as specifically described herein. Accordingly, this invention includes all modifications encompassed within the spirit and scope of the invention as defined by the following claims.

What is claimed is:

1. A method of detecting a biological material whereby a biological material is adhered to a membrane which is then contacted with a reagent capable of binding to said biological material and capable of being detected, such that the detection of said reagent bound to said biological material represents a biological material detection signal evidencing the presence of said biological material, and the detection of said reagent directly bound to said membrane represents background noise, wherein the improvement comprises utilizing a polyvinylidene fluoride membrane which has been subjected to a temperature of at least about 80° C. but less than the temperature at which the membrane softens and deforms for a time sufficient to substantially reduce said detecting reagent from directly adhering to said membrane, so as to result in a decrease in the background noise and an increase in a biological material detection signal-to-noise ratio.

2. The method of claim 1, wherein said membrane is subjected to a temperature of about 80° C. to about 160° C.

3. The method of claim 2, wherein said membrane is subjected to said temperature for about 5 minutes to about 64 hours.

4. The method of claim 1, wherein said membrane is subjected to a temperature of about 80° C. to about 150° C.

5. The method of claim 1, wherein said membrane is subjected to a temperature of about 100° C. to about 150° C.

6. The method of claim 5, wherein said membrane is subjected to said temperature for about 32 hours or more.

7. The method of claim 1, wherein said membrane is subjected to a temperature of about 120° C. to about 150° C.

8. The method of claim 7, wherein said membrane is subjected to said temperature for about 16 hours or more.

9. The method of claim 1, wherein said membrane is subjected to a temperature of about 135° C. to about 145° C.

10. The method of claim 9, wherein said membrane is subjected to said temperature for about 12 hours or more.

11. The method of claim 10, wherein said membrane is subjected to said temperature for about 24 hours or more.

12. The method of claim 1, wherein said membrane is subjected to said temperature by contacting said membrane with a heated surface.

13. The method of claim 1, wherein said membrane is subjected to said temperature by placing said membrane in a circulating air oven.

14. The method of claim 13, wherein said membrane is in the form of a roll when placed in said circulating air oven.

15. The method of claim 1, wherein said membrane is porous and has a pore rating of about 1 μm or less.

16. The method of claim 15, wherein said membrane has a pore rating of about 0.5 μm or less.

17. The method of claim 16, wherein said membrane has a pore rating of about 0.05–0.45 μm.

18. The method of claim 17, wherein said membrane has a pore rating of about 0.05–0.2 μm.

* * * * *